(12) United States Patent (10) Patent No.: US 9,186,491 B2
Casiello et al. (45) Date of Patent: Nov. 17, 2015

(54) PORT CATHETER LOCKING SYSTEM AND METHOD

(71) Applicants: Damon Casiello, Lowell, MA (US); Mark Girard, Medway, MA (US)

(72) Inventors: Damon Casiello, Lowell, MA (US); Mark Girard, Medway, MA (US)

(73) Assignee: AngioDynamics, Inc., Latham, NY (US)

( * ) Notice: Subject to any disclaimer, the term of this patent is extended or adjusted under 35 U.S.C. 154(b) by 246 days.

(21) Appl. No.: 13/860,026

(22) Filed: Apr. 10, 2013

(65) Prior Publication Data

US 2014/0309621 A1 Oct. 16, 2014

(51) Int. Cl.
*A61M 37/00* (2006.01)
*A61M 39/02* (2006.01)
*A61M 39/12* (2006.01)

(52) U.S. Cl.
CPC ........... *A61M 39/0208* (2013.01); *A61M 39/12* (2013.01)

(58) Field of Classification Search
CPC .. A61M 39/0208; A61M 39/04; A61M 39/12
USPC ........ 604/502, 288.01, 288.02, 288.04, 93.01
See application file for complete search history.

(56) References Cited

U.S. PATENT DOCUMENTS 6,527,754 B1 * 3/2003 Tallarida et al. ......... 604/288.04
2012/0065625 A1 * 3/2012 Nelson .......................... 604/533

* cited by examiner

*Primary Examiner* — Kevin C Sirmons
*Assistant Examiner* — Deanna K Hall
(74) *Attorney, Agent, or Firm* — Peter J. FLora

(57) ABSTRACT

Systems and methods for securing a catheter to an implantable port are disclosed. The system includes a collar having a catheter gripping protrusion and a port lock cavity. A port having an outlet stem with a constant cross-sectional profile is utilized. The collar is configured to mate with a port lock protrusion connected to the port.

12 Claims, 4 Drawing Sheets

A-A'

PORT CATHETER LOCKING SYSTEM AND METHOD

FIELD OF THE INVENTION

The present invention relates generally to a locking mechanism for an implantable port system. More specifically, the invention relates to a push collar and port stem configuration for securing a catheter to an implantable port.

BACKGROUND OF THE INVENTION

Implantable ports are vascular access devices commonly used to deliver or aspirate fluids to or from a target site within a patient for medical treatment. Ports generally have a reservoir that can be accessed by a needle through a self-sealing septum. The reservoir has an outlet stem that is connected to a catheter terminating at a target site within the body, such as the junction of the right atrium and the superior vena cava. The catheter is typically secured to the stem by a locking mechanism, such as a push collar or a twisting lock. The catheter can be connected to the port during various stages of the implantation process, dependent on the preferences of the medical professional performing the procedure, the specifications of the port system, and the nature of the treatment being provided.

Ports can have one or more reservoirs, the most common ports being single or dual reservoir ports. While single reservoir ports typically have a single stem for fluid communication between the reservoir and the catheter, dual reservoir ports typically have two stems arranged in an opposing D-shaped stem profile. The double D stem design features a first and second outlet from a respective first and second reservoir, merging into an opposing D-shaped stem configuration to maintain a circular profile.

Various port locking of varying geometries have been designed to ensure that the catheter remains secured to the outlet stem, and leak-free connection is maintained after implantation. For instance, snap-locks that load over a barbed outlet stem have been used to secure the port catheter. These designs usually feature interlocking elements that mate a collar and catheter to a port body via one or more barbs on the outlet stem. Alternatively, twist looks have been used, which feature a flanged locking member that mates with a void in the port body to secure the lock to the port. In other designs, locking mechanisms have included features such as resilient prongs or live hinges for engaging the locking mechanism to the port body and catheter, securing the catheter to the outlet stem.

There are however a number of drawbacks to types of locking mechanisms described above. Advancing a catheter over a barbed stem can be difficult since the catheter stretches and tightens around the barbs. Since the catheter is flexible, it often kinks as the medical professional tries to advance it over the barbs. Unsuccessful attempts to push the catheter over the barbs can lead to excessive kinking, material deformation, and premature wear and tear on the catheter, compromising its integrity and durability. Pushability of the catheter over the stem is further encumbered by the fact that the medical professional connecting the catheter to the stem is wearing sterile gloves. In addition, gloves are often wet and slippery from contact with fluids associated with performing port insertion procedures. Further, locks with engaging components such as flanges or live hinges require twisting the lock to a particular radial orientation prior to loading, so that the engaging components are in-line to mate. The complexity of these systems also adds to the profile of the locking mechanism at the catheter/port junction, increasing the footprint of the port in the port pocket. Complex locking systems also increase manufacturing and end user costs. Additionally, locking mechanisms with resilient members be less durable and more difficult to manufacture. There remains a need for an improved locking system that allows for easy catheter loading over a barb-free stem, ensures a secure and leak-free connection, is operable to engage under any radial orientation and is simple to manufacture at a low cost.

SUMMARY OF THE INVENTION

In one aspect, the invention is a port lock system having an implantable port and a collar. The port has a reservoir, a needle-penetrable septum fluidly sealing an opening to the reservoir, an outlet stem extending away from the port and in fluid communication with the reservoir, where the outlet stem has a substantially constant cross-sectional profile, and a port lock protrusion. The collar has a proximal end, a distal end and a lumen extending therebetween, a catheter gripping protrusion formed by an inner collar wall and extending into the lumen and towards a longitudinal axis centered within the lumen, and a collar lock cavity formed in the inner collar wall and extending away from the longitudinal axis. The collar lock cavity is configured to mate with the port lock protrusion.

In another aspect, the invention is a method for securing a catheter to outlet stem of an implantable port. The method includes providing a port, a catheter, and a collar. The port has a reservoir, a needle-penetrable septum fluidly sealing an opening to the reservoir, an outlet stem extending away from the port and in fluid communication with the reservoir. The outlet stem has a substantially constant cross-section, and a port lock protrusion. The collar has a proximal end, a distal end and a lumen extending therebetween, a catheter gripping protrusion formed by an inner collar wall and extending into the lumen and towards a longitudinal axis centered in the lumen, and a collar cavity formed in the inner collar wall and extending away from the longitudinal axis. The collar lock cavity is configured to mate with the port lock protrusion. The catheter has a proximal catheter end, a distal catheter end and a lumen extending therebetween. The collar is loaded over the catheter, and the proximal end of the catheter is loaded at least partially over the outlet stem. The collar is advanced proximally until the collar lock cavity mates with the port lock protrusion.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 3 illustrates catheter connection states according to an embodiment of the invention.

DETAILED DESCRIPTION OF THE INVENTION

Figure 1:
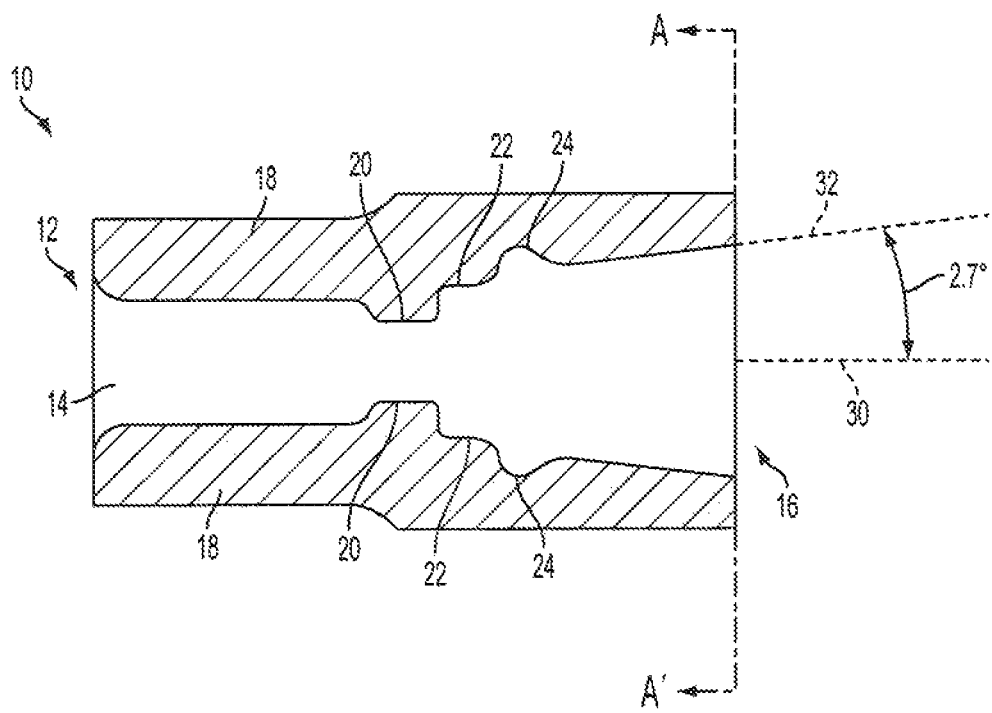
FIG. 1 is a cross-sectional view of a collar according to an embodiment of the invention.

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a locking mechanism for an implantable port.

A cross-section of a collar 10 according to an embodiment of the invention is shown in FIG. 1. The collar 10 features a proximal end 16, a distal end 12, a wall 18 and a lumen 14 extending longitudinally through the center of the collar 10. The lumen 14 is sized to accommodate a number of components including a catheter and an outlet stem. A catheter gripping protrusion 20 extends into the lumen 14, also radially surrounding the lumen 14. The surface of the catheter gripping protrusion 20 is designed to tie sufficiently narrow to squeeze into the wall of a catheter loaded over an outlet stem, securing it into place (further details on the interface between the collar components described in this paragraph and the catheter and port are explained in the disclosure referencing FIG. 4). Proximal of the catheter gripping protrusion 20 is a catheter bulge cavity 22, which is designed to accommodate the end of a flexible catheter as it bulges from compression caused by advancement over the outlet stems and contact against the port. Proximal of the catheter bulge cavity 22 is a collar lock cavity 24, which engages a corresponding port lock protrusion connected to the port for a snap lock fit. Proximal of the collar lock cavity 24 is a frustum shaped luminal section extending to the proximal opening 16, which operates as a ramp for loading the collar 10 over the port lock protrusion, providing a snap fit into a locked position. The inner side wall of the frustum shaped luminal section can flare out an angle 32 of approximately 2.7 degrees with respect to the longitudinal axis 30 of the lumen 14. Collars according to the present invention can be manufactured using materials and techniques known in the art, such as medical grade plastics formed using an injection molding process.

Figure 2:
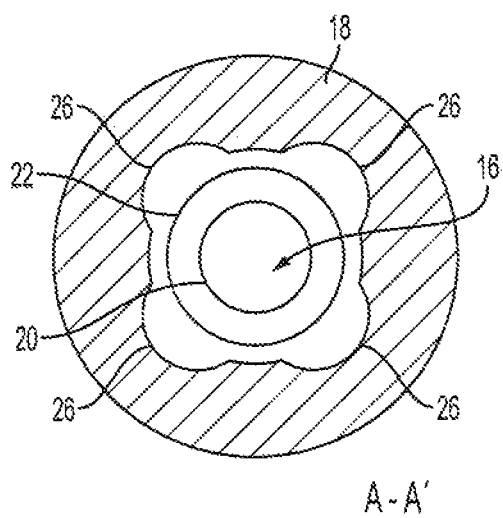
FIG. 2 is a view of the proximal end of the collar according to an embodiment of the invention.

As shown in FIG. 2, the proximal end 16 of the collar 10 can feature a number of concave surfaces 26 radially surrounding the proximal end 16 of the collar lumen 14. The concave surfaces 26 serve as relief points for the proximal 16 portion of the collar 10, so that as the collar 10 is being advanced over the port lock protrusion, the collar 10 can temporarily flex and provide snap-fit engagement into the collar lock cavity 24. The concave surfaces 26 can circumferentially surround the lumen 14 in evenly spaced increments. Although four concave surfaces 26 are shown, more or less concave surfaces can be used, such as five concave surfaces evenly spaced circumferentially around the lumen 14. Concave surfaces do not necessarily have to be contoured. For instance, the concave surface could formed from two flat surfaces meeting at an angle.

Figure 3A:
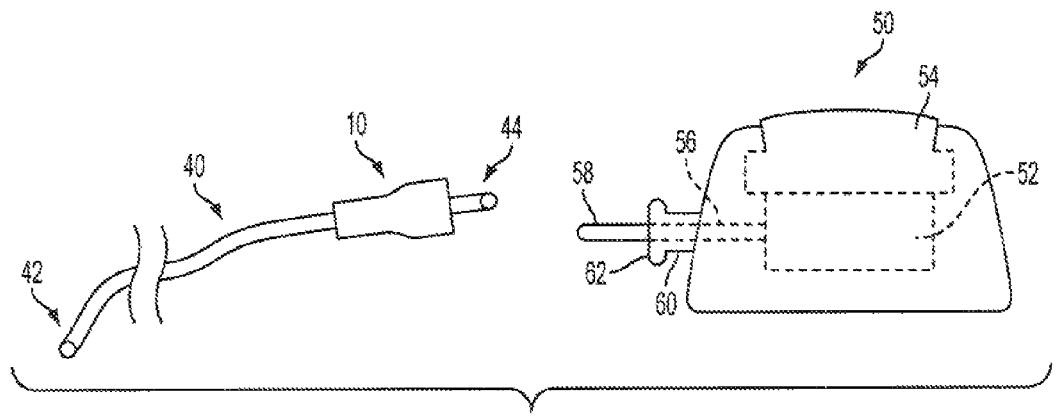
FIG. 3A shows a collar loaded over a catheter prior to connection to an outlet stem.
Figure 3B:
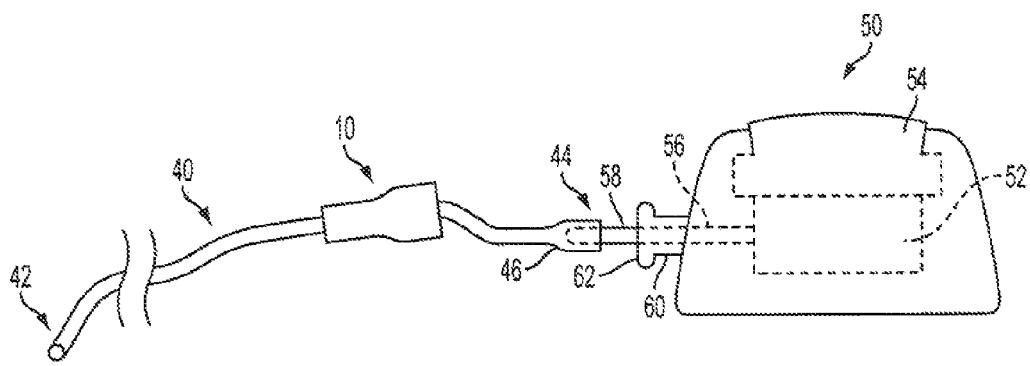
FIG. 3B shows the catheter partially loaded over an outlet stem.
Figure 3C:
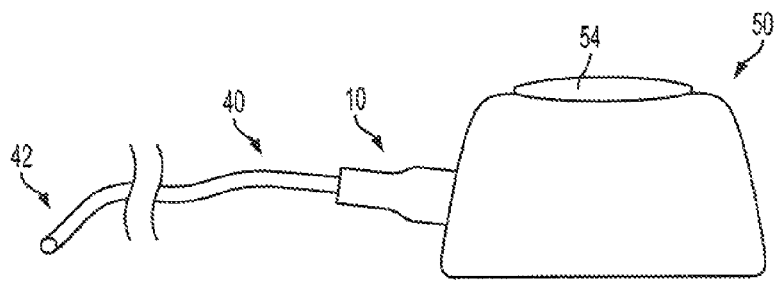
FIG. 3C shows the collar advanced over the outlet stem.

An advantage of the port lock system according to embodiments of the invention is that it is compatible with an outlet stem having a straight or non-barbed cross-sectional profile. FIGS. 3A-3C show a port lock system at various stages of loading. A port 50 has a reservoir 52, a needle penetrable septum 54, an outlet lumen 56, an outlet stem 58 and a port lock protrusion 60 having a torus shaped element 62. As shown in FIG. 3A, a collar 10 is loaded over a catheter 40 having a proximal 44 and distal 42 end. The port 50, catheter 40 and collar 10 are provided as a kit designed with geometries compatible for mating. The proximal end 44 of the catheter 40 is advanced over the distal end of the outlet stem 58. Since outlet stems according to the present invention are straight, having a linear side profile and a constant cross-sectional profile, as opposed to for instance an outlet stem having barbs, the catheter 40 can easily be advanced proximally over the outlet stem by the medical professional. Also, since the stem has a constant diameter, material deformation of the catheter can be minimized as it is being loaded. A further advantage of the invention is that even if the catheter 40 is only partially advanced over the outlet stem as shown in FIG. 3B, advancing the collar 10 over the port lock protrusion 60 as shown in FIG. 3C will fully advance the catheter 40 over the outlet stem 58. Since the gripping protrusions 20 grab the proximal end 44 of the catheter 40, advancing the collar 10 proximally will pull the catheter 40 over the remaining length of outlet stem 58, as explained in further detail with reference to FIG. 4.

Figure 4:
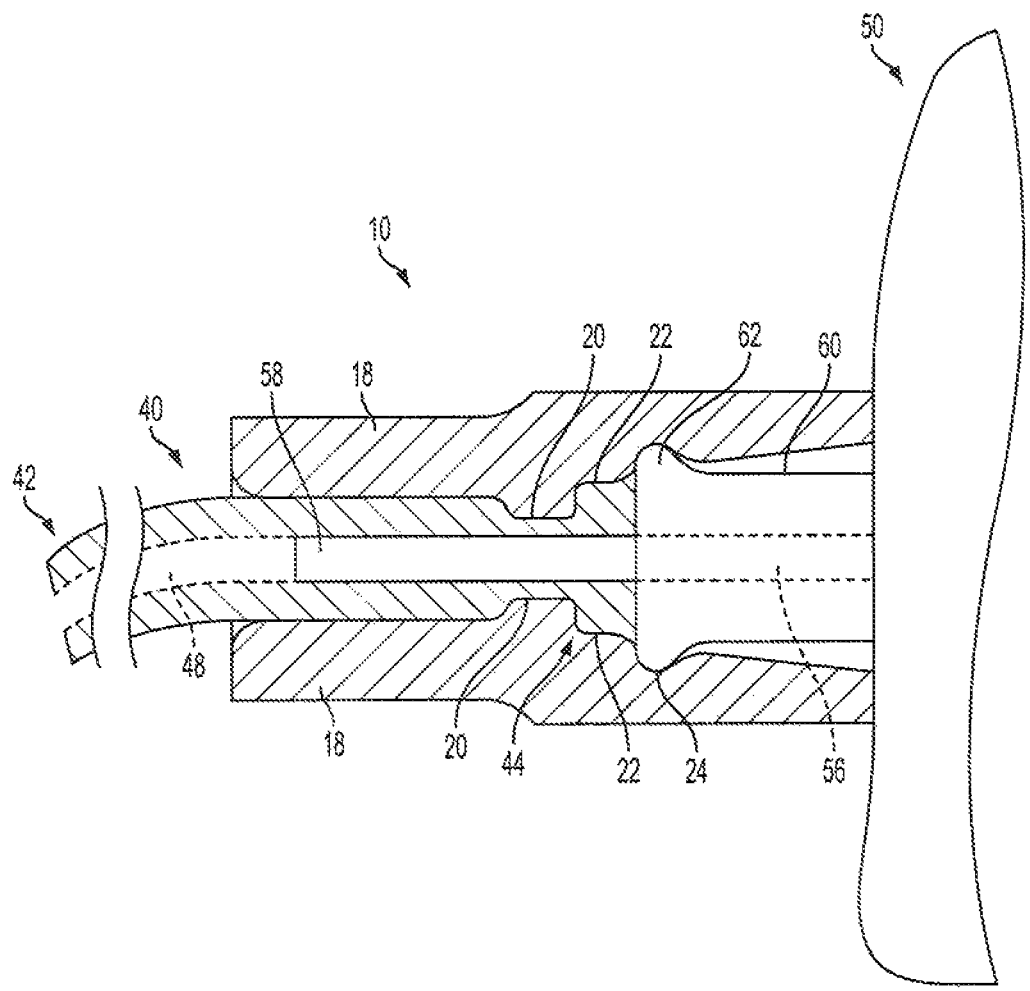
FIG. 4 is a cross-sectional view of the collar, catheter and port when the collar is engaged in locked position to the outlet stem according to an embodiment of the invention.

With reference to FIG. 4, the collar 10 and catheter 40 engaged and locked onto the outlet stem 58 of the port 50 are shown. When the collar 10 is fully advanced over the port lock protrusion 60, the torus shaped element 62 fits within the collar lock cavity 24, providing a snap-lock fit. The port lock protrusion 60 can be made of a material more rigid than the collar 10, such as a medical grade stainless steel. As mentioned above, the collar 10 also provides a catheter bulge cavity 22 to accommodate the proximal end 44 of the catheter 40. When the flexible catheter 40 is advanced proximally over the outlet stem 58 and pushed up against the distal face of the port lock protrusion 60, the proximal end 44 of the catheter 40 tends to bulge from compression forces exerted on the flexible catheter wall. Further, as illustrated in FIG. 4, catheter gripping protrusions 20 are formed so that they grip into the bulk of the catheter 40 wall, without damaging the catheter 40 wall. This grip is what allows the collar 10 to securely pull and advance the catheter 40 over the outlet stem 58 in instances where the catheter 40 is only partially pre-loaded onto the outlet stem 58 as shown in FIG. 3B. As the collar 10 is fully advanced over the port lock protrusion 60 as illustrated in FIGS. 3C and 4, the proximal end 44 of the catheter 40 becomes fully advanced onto the outlet stem 58. Dimensions of the devices can be customized based on the scale of the system, but as an illustrative example, the lumen 14 could have a diameter of approximately 0.113 inches at proximal portions of the collar 10, narrowing to approximately 0.101 inches between the catheter gripping protrusions 20. The catheter 40 wall can have a thickness of approximately 0.012 inches, so that the catheter gripping protrusions 20 press partially into the bulk of the catheter 40 wall, securing the proximal end 44 of the catheter 40 to the outlet stem 58.

Another advantage of the locking mechanism according to the present invention is that the collar does not require any particular radial orientation for proper securement. For instance, conventional twist locks may require a certain initial radial orientation so that the lock can be twisted and properly mated into a locking position. However, collars according to the present invention have locking components with geometries that radially surround the collar lumen, thus advancement of the collar under any initial radial orientation will properly allow the catheter gripping protrusions 20 and the collar lock cavity 24 to engage the catheter 40 and port lock protrusion 60.

Figure 5:
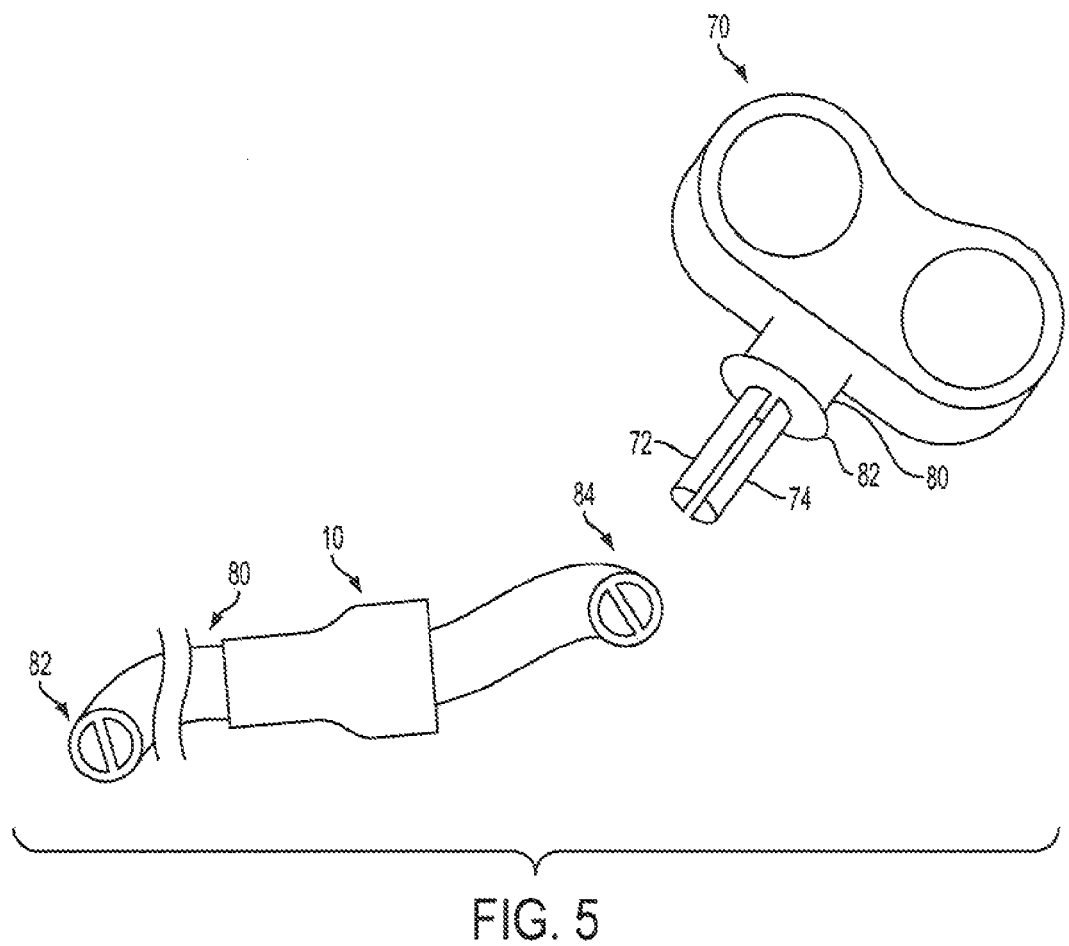
FIG. 5 is a perspective view of a dual reservoir porn dual lumen catheter and collar according to an embodiment of the invention.

Locking mechanisms according to the present invention are compatible with single and multi-reservoir port systems. A dual reservoir port system is shown in FIG. 5. The system includes a dual reservoir port 70 having a first 72 and second 74 outlet stem in fluid communication with first and second reservoirs. The port also features a port lock protrusion 80 having a torus member 82 similar to the structure described in embodiments above. The dual reservoir port 70 is compatible with a dual lumen catheter 80 having a proximal 84 and distal 82 end. As illustrated, the outlet stems 72, 74 and dual lumen catheter 80 have an opposing D-shaped lumen configuration to maintain an overall circular profile. The dual reservoir port 70 and catheter 80 are compatible with the collar 10 described in pervious embodiments, providing leak-free and secure connection.

Port lock systems according to the present invention allow medical professionals to easily and rapidly secure a catheter to the outlet stem of the port. The system can be provided in a kit that includes a port, a catheter, and a collar, as well as other components such as sterile dressings, a scalpel, an introducer, gloves, guidewires and infusion needles. At some point prior to catheter securement, the collar needs to be loaded over the catheter. In certain embodiments, the collar can be packaged in the kit pre-loaded over the catheter. The proximal end of the catheter should be loaded at least partially over the distal end of the port stem. The collar can then be advanced proximally until it slips over the port lock protrusion, snap locking the protrusion into the collar lock cavity. The collar can be loaded over the catheter either before or after the catheter is advanced over the port stem, however, for catheters using specialized distal tip configurations, it would be advantageous to load the collar prior to attaching to the catheter to the outlet stem. Trimmable port catheters are also compatible with the systems described herein, and a pre-insertion catheter measurement technique may be used to customize catheter length so that it terminates at the desired location within the body. As described above, the catheter and collar according to the present invention can be easily advanced proximally over the non-barbed outlet stem, and the collar does not require any particular radial orientation prior to advancement, providing a rapid and reliable method of securing a catheter to a port.

What is claimed is:

1. A port catheter locking system comprising:
    an implantable port comprising:
        a reservoir,
        a needle-penetrable septum fluidly sealing an opening to the reservoir,
        an outlet stem extending away from the port and in fluid communication with the reservoir, wherein the outlet stem has a substantially constant cross-sectional profile, and
        a port lock protrusion; and
    a collar comprising:
        a proximal end, a distal end and a lumen extending therebetween,
        a catheter gripping protrusion formed by an inner collar wall and extending into the lumen and towards a longitudinal axis centered within the lumen, and
        a collar lock cavity formed in the inner collar wall and extending away from the longitudinal axis;
        wherein the collar lock cavity is configured to mate with the port lock protrusion.

2. The port catheter locking system of claim 1, wherein the collar further comprises:
    a plurality of concave surfaces disposed along a proximal portion of the inner wall.

3. The port catheter locking system of claim 1, wherein the port lock protrusion comprises a torus shaped protrusion.

4. The port catheter locking system of claim 1, wherein the collar further comprises:
    a catheter bulge cavity formed in the inner collar wall and extending away from the longitudinal axis, the catheter bulge cavity disposed between the catheter gripping protrusion and the collar lock cavity.

5. The port catheter locking system of claim 1, wherein the collar further comprises:
    a frustum shaped luminal section disposed between the collar cavity and the proximal end of the collar, wherein the longitudinal axis and an inner wall of the frustum shaped luminal section assume an angle between 0.7 and 4.7 degrees.

6. The port catheter locking system of claim 5, wherein the longitudinal axis and the inner wall of the frustum shaped luminal section assume an angle of approximately 2.7 degrees.

7. A method for securing a catheter to an outlet stem of an implantable port, the method comprising:
    providing a port, a catheter, and a collar,
        the port comprising a reservoir, a needle-penetrable septum fluidly sealing an opening to the reservoir, an outlet stem extending away from the port and in fluid communication with the reservoir, wherein the outlet stem has a substantially constant cross-section, and a port lock protrusion,
        the collar comprising a proximal end, a distal end and a lumen extending therebetween, a catheter gripping protrusion formed by an inner collar wall and extending into the lumen and towards a longitudinal axis centered in the lumen, and a collar cavity formed in the inner lock wall and extending away from the longitudinal axis, wherein the collar lock cavity is configured to mate with the port lock protrusion, and
        the catheter comprising a proximal catheter end, a distal catheter end and a lumen extending therebetween;
    loading the collar over the catheter;
    loading the proximal end of the catheter at least partially over the outlet stem;
    advancing the collar proximally until the collar lock cavity mates with the port lock protrusion.

8. The method of claim 7, wherein the collar further comprises:
    a plurality of concave surfaces disposed along a proximal portion of the inner wall.

9. The method of claim 7, wherein the port lock protrusion comprises a torus shaped protrusion.

10. The method of claim 7, wherein the collar further comprises:
    a catheter bulge cavity formed in the inner collar wall and extending away from the longitudinal axis, the catheter bulge cavity disposed between the catheter gripping protrusion and the collar lock cavity.

11. The method of claim 7, wherein the collar further comprises:
    a frustum shaped luminal section disposed between the collar cavity and the proximal end of the collar, wherein the longitudinal axis and an inner wall of the frustum shaped luminal section assume an angle between 0.7 and 4.7 degrees.

12. The method of claim 11, wherein the longitudinal axis and the inner wall of the frustum shaped luminal section assume an angle of approximately 2.7 degrees.

* * * * *